United States Patent
Graziano

(10) Patent No.: US 8,951,284 B2
(45) Date of Patent: Feb. 10, 2015

(54) ANESTHETIC SUTURE

(71) Applicant: Thomas Graziano, Clifton, NJ (US)

(72) Inventor: Thomas Graziano, Clifton, NJ (US)

( * ) Notice: Subject to any disclaimer, the term of this patent is extended or adjusted under 35 U.S.C. 154(b) by 201 days.

(21) Appl. No.: 13/707,711

(22) Filed: Dec. 7, 2012

(65) Prior Publication Data

US 2014/0163611 A1   Jun. 12, 2014

(51) Int. Cl.
*A61B 17/04* (2006.01)
*A61L 17/00* (2006.01)
*A61B 17/06* (2006.01)

(52) U.S. Cl.
CPC ......... *A61L 17/005* (2013.01); *A61B 17/06166* (2013.01); *A61L 2300/402* (2013.01)
USPC ...................................................... 606/228

(58) Field of Classification Search
CPC ..................... A61B 17/0401; A61B 17/06166; A61B 2017/0414; A61B 2017/044
USPC .......... 606/224–232, 139, 148, 153, 151, 144
See application file for complete search history.

(56) References Cited

U.S. PATENT DOCUMENTS

| | | | |
|---|---|---|---|
| 5,458,582 A | 10/1995 | Nakao | |
| 5,919,473 A * | 7/1999 | Elkhoury | 424/422 |
| 6,689,153 B1 * | 2/2004 | Skiba | 606/232 |
| 8,257,393 B2 | 9/2012 | Cichocki, Jr. | |
| 8,273,104 B2 | 9/2012 | Cohen | |
| 2002/0055759 A1 | 5/2002 | Shibuya | |
| 2005/0125034 A1 * | 6/2005 | Cichocki | 606/222 |
| 2006/0182778 A1 | 8/2006 | Balar et al. | |
| 2010/0274282 A1 * | 10/2010 | Olson | 606/228 |
| 2013/0317545 A1 * | 11/2013 | Gross et al. | 606/230 |

* cited by examiner

*Primary Examiner* — Jocelin Tanner
(74) *Attorney, Agent, or Firm* — Thomas J. Germinario

(57) ABSTRACT

A multi-filament surgical suture comprising cover and core layers is differentially coated or impregnated with a long-acting local anesthetic so as produce a differential distribution of the anesthetic within the suture. The differential distribution of the anesthetic within the suture can be adjusted so as to release a uniform or variable prescribed dosage of the anesthetic at a uniform or variable prescribed rate over one or more prescribed intervals. The time-release period and the rate of anesthetic release can be regulated to suit the needs of the specific patient and/or the nature of the surgical procedure.

6 Claims, 3 Drawing Sheets

ANESTHETIC SUTURE

BACKGROUND OF THE INVENTION

The present invention relates to the fields of surgical sutures and local anesthetics, and more particularly to the field of surgical sutures that contain a local anesthetic, which is released from the sutures to relieve post-operative pain.

Prior to the closure of an incision in surgery, a local anesthetic is usually injected into the operative site to relieve post-operative pain. The effective duration of the surgically-applied local anesthetic is, however, quite limited, often less than six hours. After the surgically-applied local anesthetic becomes ineffective, a narcotic analgesic which acts on the central nervous system, such as morphine, must be administered to the patient. But narcotic analgesics have adverse side effects, including loss of alertness, respiratory complications, nausea, and possible addiction.

It is therefore desirable to minimize the use of narcotic analgesics to treat post-operative pain. One method of doing this is to incorporate a local anesthetic into the surgical sutures used at the operative site. In this way, the local anesthetic can be released over a longer duration as the suture material dissolves and is absorbed by the surrounding tissue. It is also desirable to have a method of regulating the dosage and release rate of the anesthetic from the suture, since different surgical procedures will require varying degrees and durations of post-operative pain relief.

One approach to anesthetic sutures is to provide an "active suture", where the suture is hollow and is connected to an external anesthetic delivery device, such as an injection pump, a syringe, or an IV. Examples of such "active sutures" are disclosed in the U.S. patents of Nakao (U.S. Pat. No. 5,458,582) and Cichocki, Jr. (U.S. Pat. No. 8,257,393). While the rate and duration of drug administration is controllable using these devices, that control requires active intervention of a medical professional, and end portions of the sutures must be left protruding from the operative site.

Another approach is to provide an anesthetic coating on the sutures, so that the local anesthetic leaches over time into the operative site. Examples of coated sutures are taught in the U.S. patents of Skiba (U.S. Pat. No. 6,689,153) and Cohan (U.S. Pat. No. 8,273,104), and in the U.S. patent applications of Shibuya (2002/0055759) and Balar et al. (2006/0182778). But these uniformly coated sutures lack any mechanism for controlling the rate at which the anesthetic is released and the duration of the release.

The present invention, on the other hand uses a differentially coated/impregnated multifilament or braided filament suture material to adjust the time-release period and the rate of anesthetic release to suit the needs of the specific patient and/or the nature of the surgical procedure.

SUMMARY OF THE INVENTION

Surgical sutures are fabricated from a variety of materials, including polymers. Structurally, they can be monofilaments or braided multi-filaments. For a suture that has been coated or impregnated with a therapeutic substance, the rate and duration of substance release from the suture is directly proportional to the concentration of the substance in the suture. For a uniformly coated/impregnated suture, therefore, the release rate will gradually diminish over time as the concentration of the substance in the suture decreases.

In the present invention, however, a braided multi-filament suture is used, and the individual filaments are coated or impregnated so that they have a range of anesthetic concentrations. The filaments are then braided such that filaments with certain selected concentrations have more exposure to the outer surface of the suture and/or to the internal interstices of the braid. For example, if it were desirable to have a uniform dosage of anesthetic released at a constant rate, the filaments having lower concentrations of anesthetic would be located along the outer surface of the braided suture, while mid-level concentrations would surround the interstices and filaments with the highest anesthetic concentrations would be grouped in the core filaments. If, on the other hand, it were necessary to release a very high dosage of anesthetic initially, and then a diminishingly lower level over time, the filaments having the highest concentrations of anesthetic would be located along the outer surface of the braided suture, while filaments with the lower concentrations and greater volume of the anesthetic would be grouped along the interstices and in the core of the suture. In a third scenario, the peak dosage could be delayed by locating the filaments with the highest concentrations of anesthetic in proximity to the interstices and/or the core of the braided suture.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

DETAILED DESCRIPTION OF THE PREFERRED EMBODIMENTS

Figure 1:
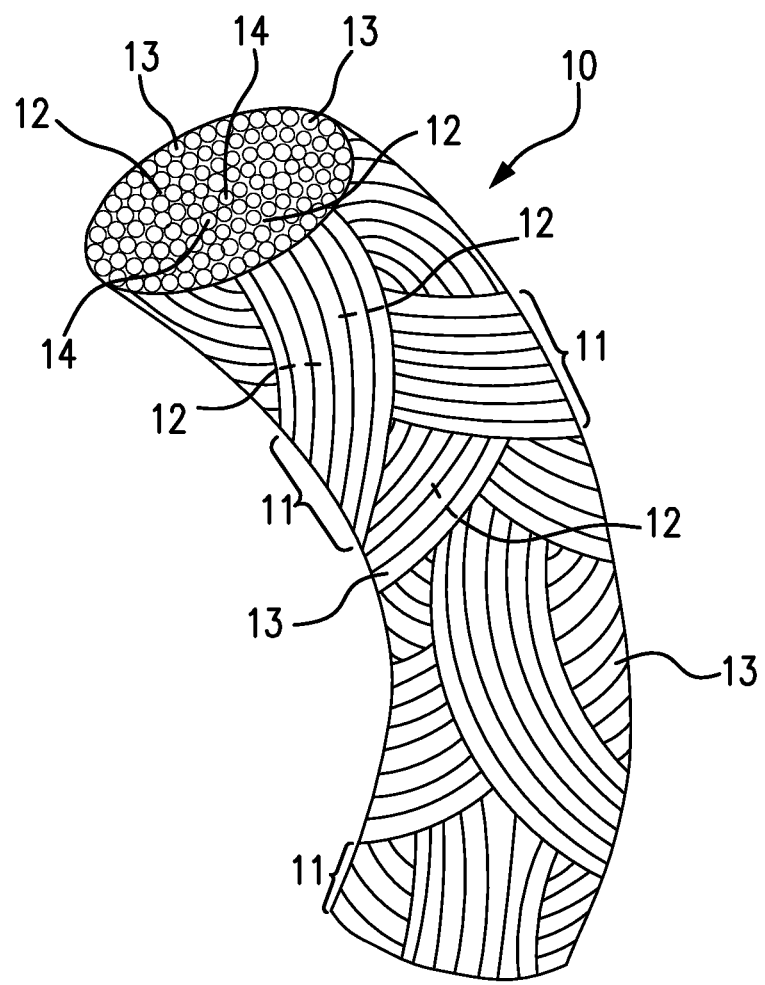
FIG. 1 is a perspective view of a braided anesthetic suture strand according to the first preferred embodiment of the present invention.

Referring to FIG. 1, the first preferred embodiment of the present invention applies to an integrally braided surgical suture, i.e. one in which is not divided into distinct cover and core elements. The surgical suture strand 10 comprises multiple interwoven braids 11 having interstices 12 between the braids 11. The braids 11 consist of bundles of filaments, some of which are surface filaments 13 and some of which are core filaments 14. The surface filaments 13, the core filaments 14 and the interstices 12 are differentially impregnated or coated with a long-acting local anesthetic, such a bupivacaine, so as to regulate the rate and duration of release of the anesthetic from the suture strand 10. The rate and duration of anesthetic release can be regulated to comport with the type and level of pain relief required by a specific surgical procedure and/or the particular needs of the patient.

For example, for cases which call for an initial high dosage of local anesthetic followed by a sustained lower dosage, the surface filaments 13 will contain a higher concentration of the local anesthetic, which will be quickly released into the surrounding tissues, while the core filaments 14 will contain a lower concentration but greater volume of the anesthetic, so that the release of the lower dosage is extended over time. In order to provide a transition between the high dosage and lower dosage anesthetic release, the interstices 12 can contain a lesser volume intermediate concentration of the local anesthetic.

Figure 2:
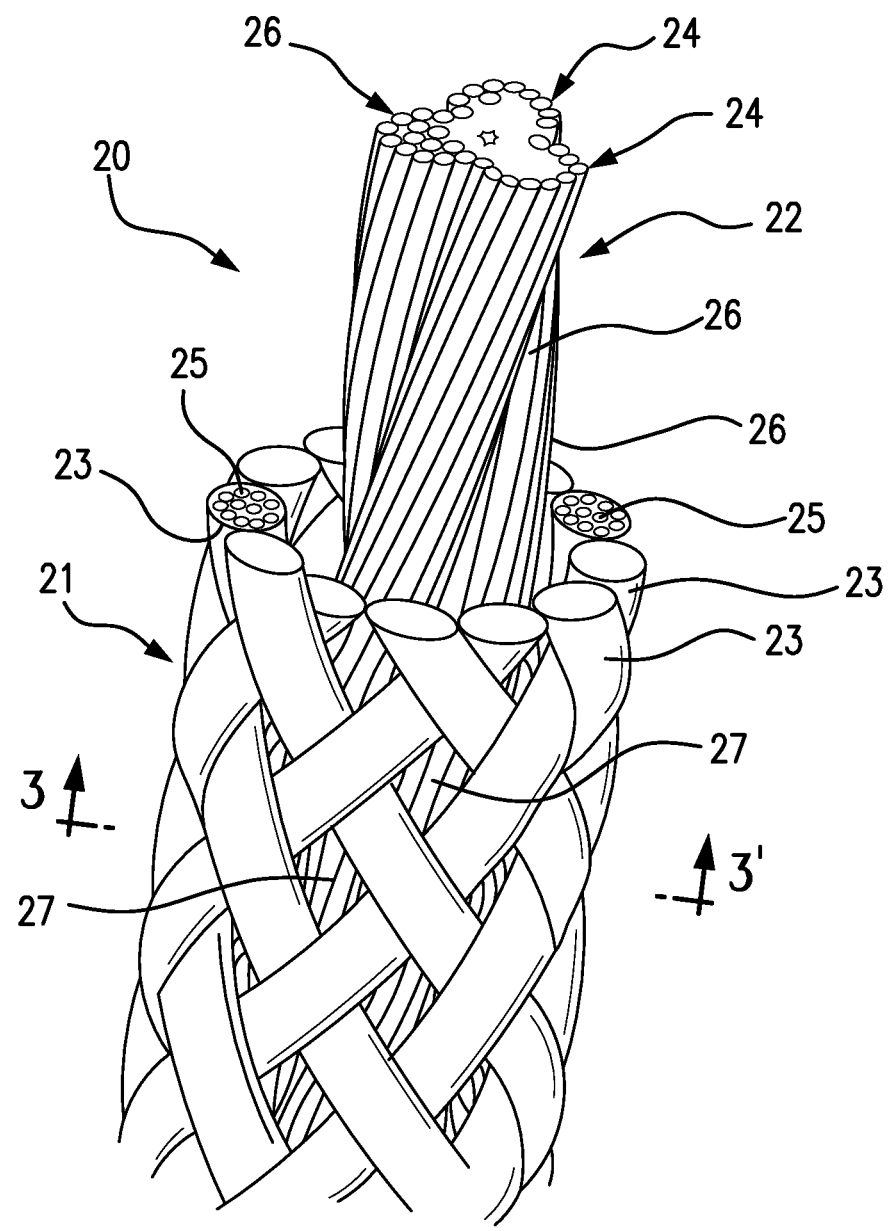
FIG. 2 is a perspective view, partially broken away, of a braided anesthetic suture strand according to the second preferred embodiment of the present invention.
Figure 3:
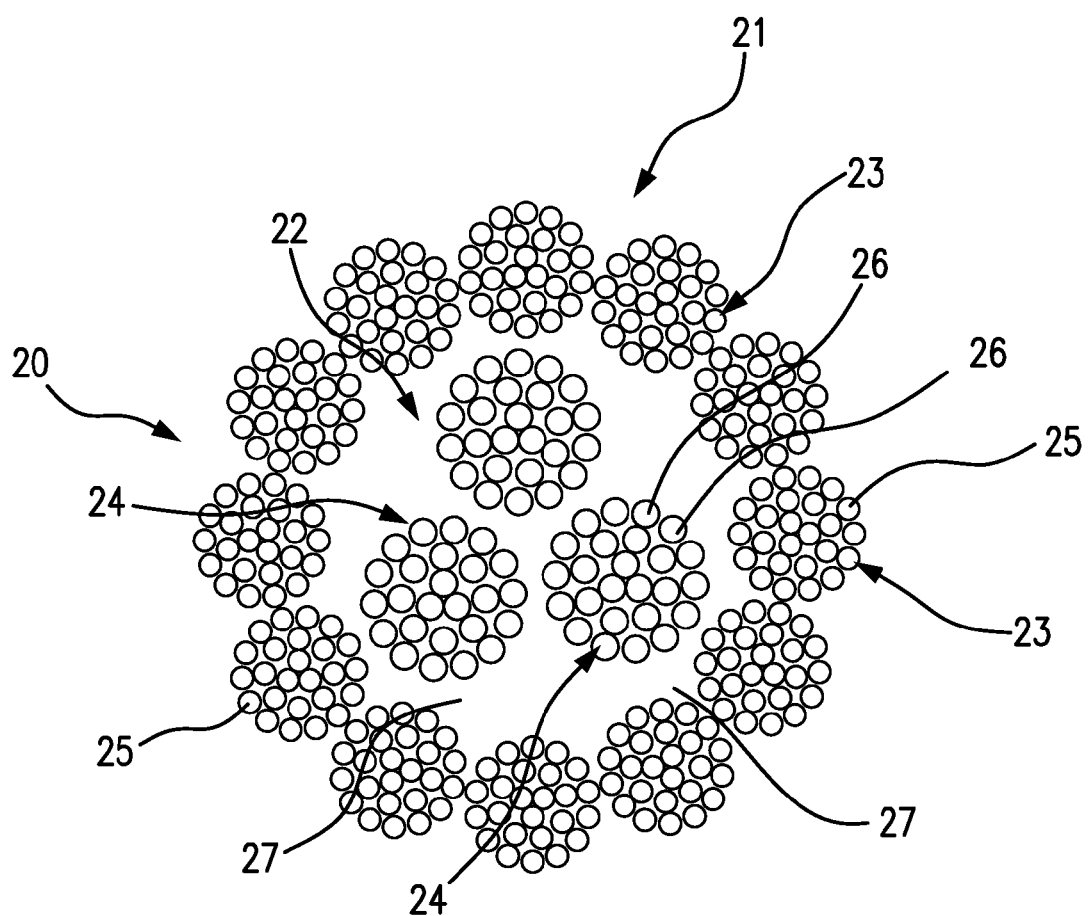
FIG. 3 is a cross-sectional view of the braided anesthetic suture strand of FIG. 2, taken along the plane 3-3'.

Referring now to FIGS. 2 and 3, the second preferred embodiment of the present invention applies to a multi-layered braided surgical suture, in which each strand 10 consists of a core 22 surrounded by a cover 21. The cover 21 comprises multiple interwoven cover braids 23, and the core 22 similarly comprises multiple interwoven or intertwined core braids 24. The cover braids 23 and the core braids 24 are composed, respectively, of multiple cover filaments 25 and core filaments 26. Between the individual cover braids 23 and also between the cover 21 and the core 22, there are multiple interstices 27. The cover braids 23 and the core braids 24 are differentially impregnated or coated with a long-acting local anesthetic, such a bupivacaine, so as to regulate the rate and duration of release of the anesthetic from the suture strand 10. The rate and duration of anesthetic release can be regulated to comport with the type and level of pain relief required by a specific surgical procedure and/or the particular needs of the patient.

For example, for cases which call for a uniform dosage of local anesthetic over an extended time period, the cover braids 23 will contain a lower concentration of the local anesthetic, which will be quickly released into the surrounding tissues, while the core braids 24 will contain a higher concentration and a greater volume of the anesthetic, so that the release of the local anesthetic is sustained over time at a constant level. In order to provide a transition between the initial and extended periods of anesthetic release, the interstices 12 can contain a lesser volume intermediate concentration of the local anesthetic.

Although the preferred embodiment of the present invention has been disclosed for illustrative purposes, those skilled in the art will appreciate that many additions, modifications and substitutions are possible, without departing from the scope and spirit of the present invention as defined by the accompanying claims.

What is claimed is:

1. An anesthetic suture, comprising:
multiple interwoven braids consisting of bundles of filaments;
wherein the suture has an outer surface and an inner core;
wherein multiple surface filaments are exposed at the outer surface of the suture, and multiple core filaments are within the core of the suture;
wherein multiple interstices are located between the braids;
wherein individual filaments of the interstices, the surface filaments and the core filaments are differentially impregnated or coated with a long-acting local anesthetic, so as to produce a differential distribution of the anesthetic within the suture, such that sections forming the interstices, the surface filaments and the core filaments each contain a different concentration and volume of the anesthetic and each release the anesthetic at a different rate and for a different duration; and
wherein the differential distribution of the anesthetic within the suture can be adjusted so as to release a uniform or variable prescribed dosage of the anesthetic at a uniform or variable prescribed rate over one or more prescribed intervals.

2. The anesthetic suture according to claim 1, wherein the local anesthetic is bupivacaine.

3. An anesthetic suture, comprising:
multiple interwoven braids consisting of bundles of filaments;
wherein the suture has an outer cover and an inner core;
wherein the cover comprises multiple cover braids and the core comprises multiple core braids;
wherein multiple interstices are located between the cover braids and between the cover and the core;
wherein individual filaments of the interstices, the cover braids and the core braids are differentially impregnated or coated with a long-acting local anesthetic, so as to produce a differential distribution of the anesthetic within the suture, such that section forming the interstices, the cover braids and the core braids each contain a different concentration and volume of the anesthetic and each release the anesthetic at a different rate and for a different duration; and
wherein the differential distribution of the anesthetic within the suture can be adjusted so as to release a uniform or variable prescribed dosage of the anesthetic at a uniform or variable prescribed rate over one or more prescribed intervals.

4. The anesthetic suture according to claim 3, wherein the local anesthetic is bupivacaine.

5. An anesthetic suture, comprising:
multiple filaments or bundles of filaments;
wherein the suture has an outer surface and an inner core;
wherein multiple surface filaments are exposed at the outer surface of the suture, and multiple core filaments are within the core of the suture;
wherein multiple interstices are located between the filaments;
wherein individual filaments of the interstices, the surface filaments and the core filaments are differentially impregnated or coated with a long-acting local anesthetic, so as to produce a differential distribution of the anesthetic within the suture, such that section forming the interstices, the surface filaments and the core filaments each contain a different concentration and volume of the anesthetic and each release the anesthetic at a different rate and for a different duration; and
wherein the differential distribution of the anesthetic within the suture can be adjusted so as to release a uniform or variable prescribed dosage of the anesthetic at a uniform or variable prescribed rate over one or more prescribed intervals.

6. The anesthetic suture according to claim 5, wherein the local anesthetic is bupivacaine.

* * * * *